United States Patent [19]

Unger et al.

[11] Patent Number: 5,694,940
[45] Date of Patent: Dec. 9, 1997

[54] APPARATUS AND METHOD FOR PROVIDING DUAL OUTPUT SIGNALS IN A TELEMETRY TRANSMITTER

[75] Inventors: John David Unger, Windham, N.H.; Mark Edward Kolnsberg; Wolfgang Scholz, both of Beverly, Mass.

[73] Assignee: Siemens Medical Systems, Inc., Iselin, N.J.

[21] Appl. No.: 574,594

[22] Filed: Dec. 19, 1995

Related U.S. Application Data

[63] Continuation-in-part of Ser. No. 40,697, Mar. 31, 1993, abandoned.

[51] Int. Cl.$^6$ .............................................. A61B 5/0402
[52] U.S. Cl. ................................... 128/696; 128/903
[58] Field of Search ................................. 128/696, 697, 128/903

[56] References Cited

U.S. PATENT DOCUMENTS

| | | | |
|---|---|---|---|
| 3,603,881 | 9/1971 | Thornton | 325/30 |
| 3,646,606 | 2/1972 | Buxton et al. | 128/2.06 R |
| 3,709,212 | 1/1973 | Koeblitz | 128/696 |
| 3,724,455 | 4/1973 | Unger | 128/2.06 A |
| 3,882,277 | 5/1975 | DePedro et al. | 179/2 DP |
| 3,923,041 | 12/1975 | Stasz et al. | 128/697 |
| 3,986,498 | 10/1976 | Lewis | 128/2.06 R |
| 4,577,639 | 3/1986 | Simon et al. | 128/696 |
| 4,658,831 | 4/1987 | Reinhard et al. | 128/697 |
| 4,934,376 | 6/1990 | Armington | 128/696 |
| 4,974,600 | 12/1990 | Reyes | 128/696 |
| 4,981,141 | 1/1991 | Segalowitz | 128/696 |
| 5,025,808 | 6/1991 | Hafner | 128/696 |
| 5,085,224 | 2/1992 | Galen et al. | 128/903 |
| 5,231,990 | 8/1993 | Gauglitz | 128/697 |
| 5,307,817 | 5/1994 | Guggenbuhl et al. | 128/696 |
| 5,417,222 | 5/1995 | Dempsey et al. | 128/696 |

FOREIGN PATENT DOCUMENTS

| | | | |
|---|---|---|---|
| 2591464 | of 0000 | France . | |
| 88/05282 | 7/1988 | WIPO . | |
| 8805282 | 7/1988 | WIPO | 128/696 |

OTHER PUBLICATIONS

Siemens "SIRECUST 1481 T" brochure.
Siemens "SIRECUST 630" brochure.

*Primary Examiner*—William E. Kamm
*Attorney, Agent, or Firm*—Lawrence C. Edelman

[57] ABSTRACT

Telemetry transmitting apparatus and a method are provided for reception and transmission of heart related electrical signals, such as electrocardiogram (EKG) and/or cardiac pacemaker signals, from a plurality of electrodes coupled to the body of a medical patient. A receiving facility of the apparatus receives a plurality of analog signals representing at least the EKG signals. An output signal representing the EKG signals is formed and transmitted, via a wireless coupling, to a telemetry receiver. An analog output port is provided on the telemetry transmitting apparatus. The analog output port is also coupled to the receiving facility. A plurality of output signals representing the EKG signals is provided to the analog output port of the telemetry transmitting apparatus. The analog output port may be coupled to buffers at the input terminals of the apparatus. Alternatively, the output port may receive processed signals from the amplifier in the telemetry transmitter that are gain adjusted to emulate the unprocessed voltage signals of the EKG electrodes and then combined with a digital pace pulse signal so that the output signals include pacemaker pulse information.

20 Claims, 4 Drawing Sheets

APPARATUS AND METHOD FOR PROVIDING DUAL OUTPUT SIGNALS IN A TELEMETRY TRANSMITTER

CROSS REFERENCE TO RELATED APPLICATIONS

This application is a continuation-in-part of U.S. application Ser. No. 08/040,697, filed Mar. 31, 1993 now abandoned.

FIELD OF THE INVENTION

The present invention relates to apparatus and methods for distributing data from a medical patient by way of a telemetry transmitting device.

BACKGROUND OF THE INVENTION

Telemetry transmitters provide a convenient means for remotely monitoring the medical condition of a patient, i.e., monitoring heart related electrical signals, such as electrocardiogram (EKG) and cardiac pacemaker signals. The telemetry transmitter is connected to the patient by electrodes and wires. The telemetry transmitter includes terminals for receiving the EKG and pacemaker signals from the wires, and a wireless transmitter that comprises, for example, a radio frequency (RF) link. Additional circuitry may be provided in the transmitter device for amplifying, filtering and multiplexing the received EKG and pacemaker signals. The transmitter sends the EKG and pacemaker signals to a telemetry receiver, which is typically in a central station.

It is often desirable to monitor the EKG and pacemaker signals locally. For example, a doctor or nurse may wish to review the EKG and/or the pacemaker signals while making his or her rounds. In some Telemetry transmitters, such as the model 1481T Telemetry transmitter manufactured by the Siemens Corporation, a display is provided for locally monitoring the EKG signals. Although this provides convenience, it increases the cost of the telemetry transmitter.

An alternative method that allows local monitoring is to place a telemetry receiver in the patient's room and connect the telemetry receiver to a monitor, as is done at the central station. While convenient, this is also quite expensive. U.S. Pat. No. 3,882,277 to DePedro et al. describes such a telemetry system. A telemetry receiver is placed in the patient's room, and the receiver is connected to a modem for transmission over a conventional telephone system.

If the hospital has an EKG monitor available (for example, a mobile transport monitor), the EKG electrodes that are attached to the patient could be disconnected from the telemetry transmitter and reconnected to the transport monitor for in-room monitoring. This method is cost effective, but is inconvenient, because the patient's EKG signal is not received at the central station while the EKG electrodes are connected to the transport monitor. This method also requires that the caregiver perform four steps including: (1) disconnecting the electrodes from the telemetry transmitter; (2) connecting the electrodes to the transport monitor; (3) disconnecting the electrodes from the transport monitor, when local monitoring is completed; and (4) reconnecting the electrodes to the telemetry transmitter. Performing these steps takes up the caregiver's valuable time.

Another problem associated with the method described above could occur while monitoring the quality of the electrode contacts. The quality of the EKG and pacemaker waveforms is affected by the quality of the electrode contact to the skin, so viewing the EKG and/or pacemaker waveforms from the bedside monitor via the telemetry transmitter allows evaluation of the electrode contact in the patient's room. Using the method described in the previous paragraph, the electrode contact may be disturbed while performing steps (3) and (4). The caregiver would not immediately become aware of this problem because he or she would no longer be viewing the waveform on the transport monitor. The discrepancy would not be detected until someone viewed the waveform back at the central station. At that point, it would be necessary to dispatch another person back to the patient's room to fix the electrode contact.

A convenient, low cost apparatus for locally monitoring the output of an EKG telemetry transmitter is desired.

SUMMARY OF THE INVENTION

The present invention is embodied in telemetry transmitting apparatus and a method for reception and transmission of medical data representing a medical condition of a patient, i.e., heart related electrical signals, such as electrocardiogram (EKG) and/or cardiac pacemaker signals. The signals are received from a plurality of electrodes coupled to the body of a medical patient.

A receiving facility of the apparatus receives a plurality of analog signals representing at least the EKG signals. An output signal representing the EKG signals is formed and transmitted, via a wireless coupling, to a telemetry receiver.

An analog output port is provided on the telemetry transmitting apparatus. The analog output port is also coupled to the receiving facility. A plurality of output signals representing the EKG signals is provided to the analog output port of the telemetry transmitting apparatus. The output signals provided to the analog output port of the telemetry transmitting apparatus, as well as those transmitted via the wireless coupling, may also represent the cardiac pacemaker signals.

DETAILED DESCRIPTION OF THE INVENTION

Figure 1:
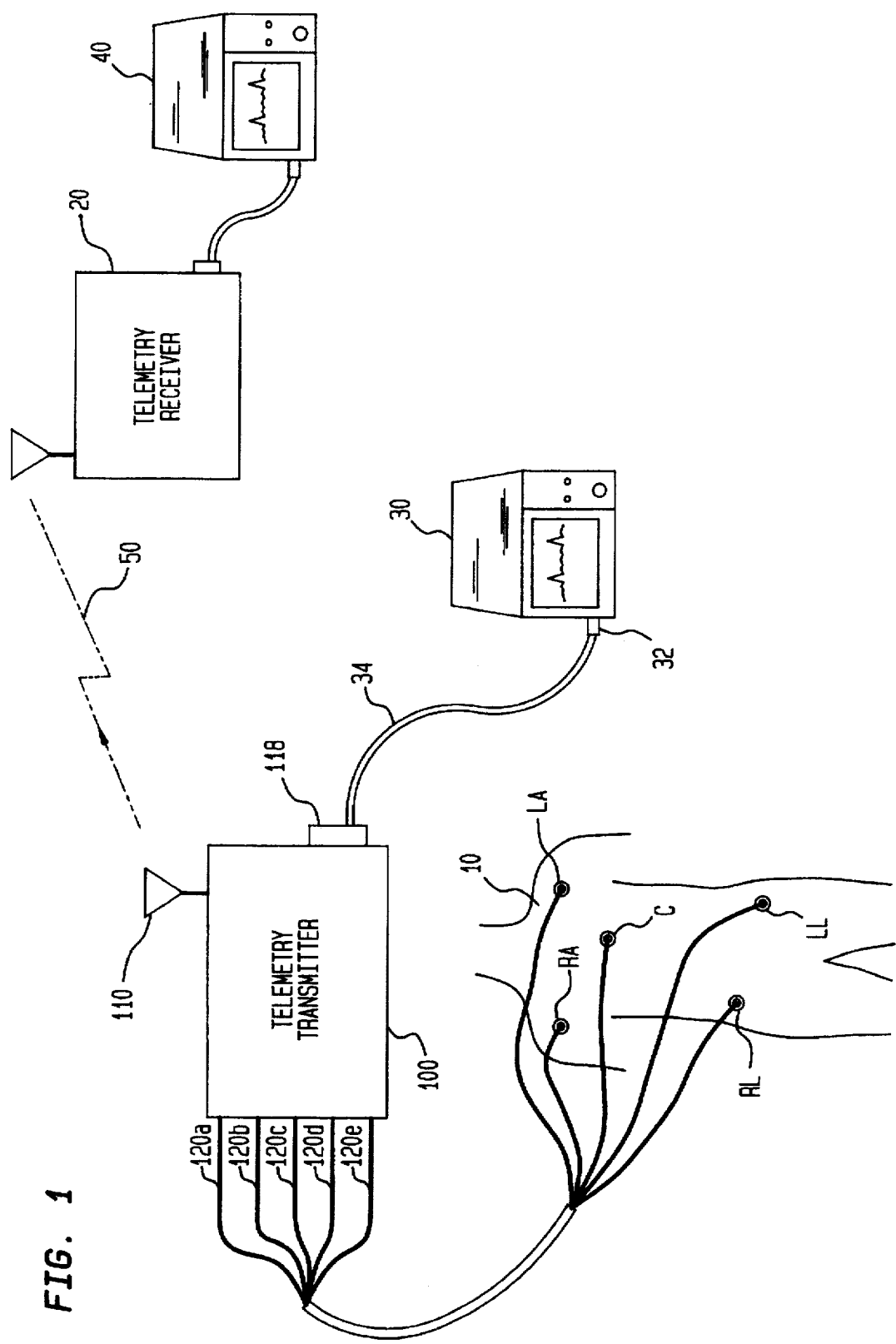
FIG. 1 is a block diagram of an exemplary system according to the invention.

FIG. 1 is a block diagram of an exemplary system including a telemetry transmitting apparatus 100 according to the invention. The telemetry transmitting apparatus 100 receives a plurality of analog signals representing the patient's condition, which may be, for example heart related electrical signals, such as electrocardiogram (EKG) waveform signals and pacemaker pulse signals acquired by a plurality of electrodes 120a–e coupled to the body of a medical patient 10. The transmitter provides means for forming and transmitting an output signal 50 representing the EKG and pacemaker waveforms, via a wireless coupling to a telemetry receiver 20. The telemetry receiver 20 may be of a conventional type, and may be coupled to a central station 40 for monitoring the patient's condition remotely.

In accordance with the invention, the telemetry transmitter 100 also includes an analog output port 118, which provides a plurality of analog output signals representing the EKG waveforms and pacemaker pulses. An electrical cable 34 may be used to connect the analog output port 118 of the telemetry transmitting apparatus 100 to the input port 32 of a monitor 30 in the patient's room. To view the EKG signals without the pacemaker pulses, monitor 30 may be any patient monitor capable of receiving EKG electrodes. To view the EKG signals with the pacemaker pulses, monitor 30 must be able to sense pacemaker spikes. For example, monitor 30 may be a conventional transport monitor, such as the SIRECUST 630 transport monitor, manufactured by Siemens corporation.

Using the analog output port 118, a medical caregiver can easily connect a monitor 30, to the telemetry transmitter 100 without the need to disconnect the electrodes 120a–e from transmitter 100. The process of connecting the transmitter 100 to the monitor 30 only involves the single step of connecting the cable 34 to the output port 118 and the input port 32. Similarly, disconnecting monitor 30 is performed in a single step. There is no interruption in transmitting signal 50 to the telemetry receiver 20 for remote monitoring during any of the periods when monitor 30 is being connected, when the patient's EKG with pacemaker activity is viewed locally, or when the monitor 30 is being disconnected. The EKG signals may be monitored locally, on monitor 30, and remotely, on monitor 40, at the same time.

Another benefit of the invention is that the caregiver can verify the quality of the EKG waveform that is transmitted by the telemetry transmitter 100, without disturbing any existing connections. There is no need to disturb the electrodes to perform this evaluation. Cable 34 is connected to port 118 of the telemetry transmitter 100 to start local monitoring; and the cable 34 is unplugged from the port 118 when local monitoring is completed.

Figure 2:
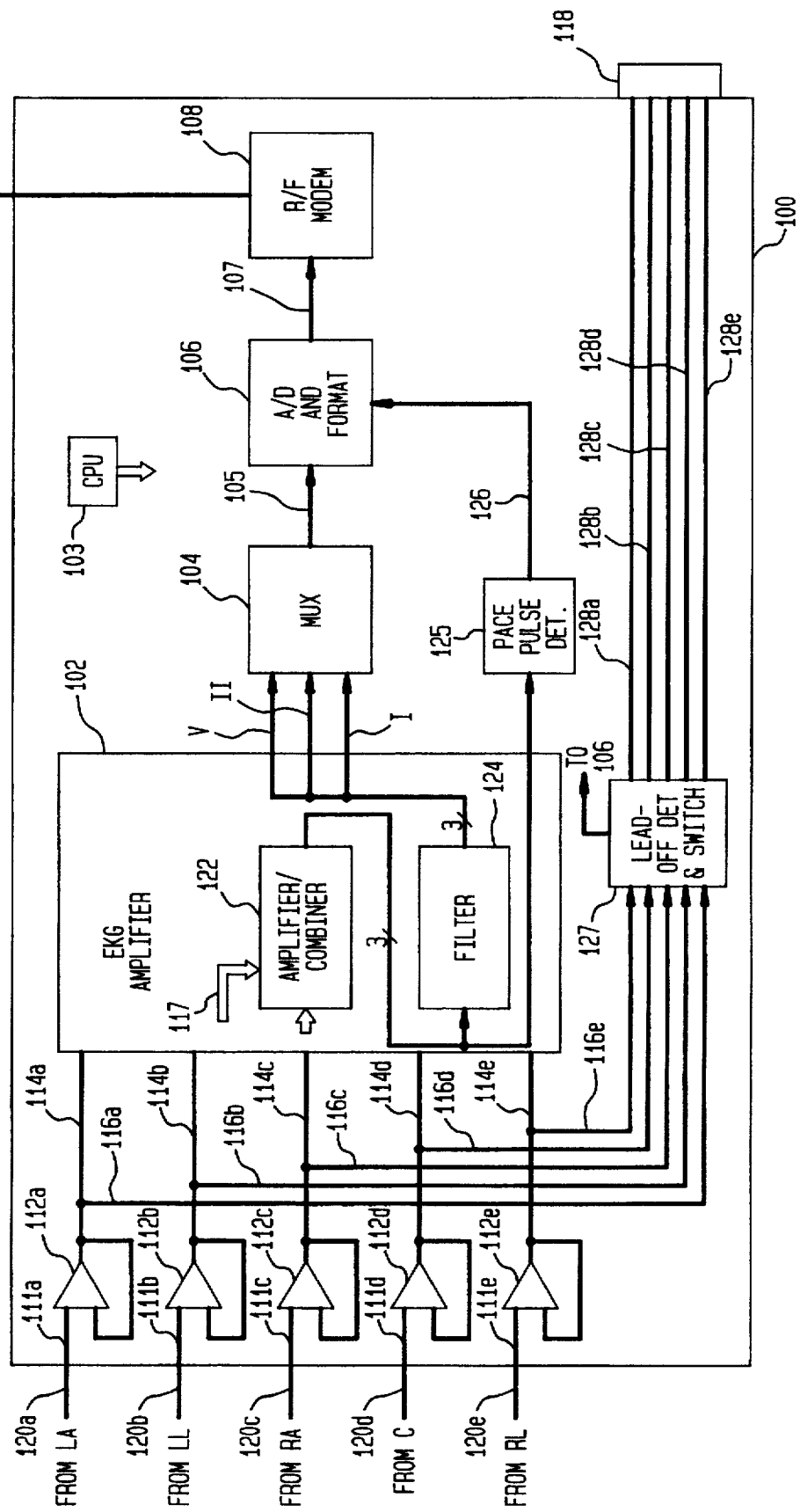
FIG. 2 is a block diagram of an exemplary embodiment of the telemetry transmitter shown in FIG. 1.
Figure 3:
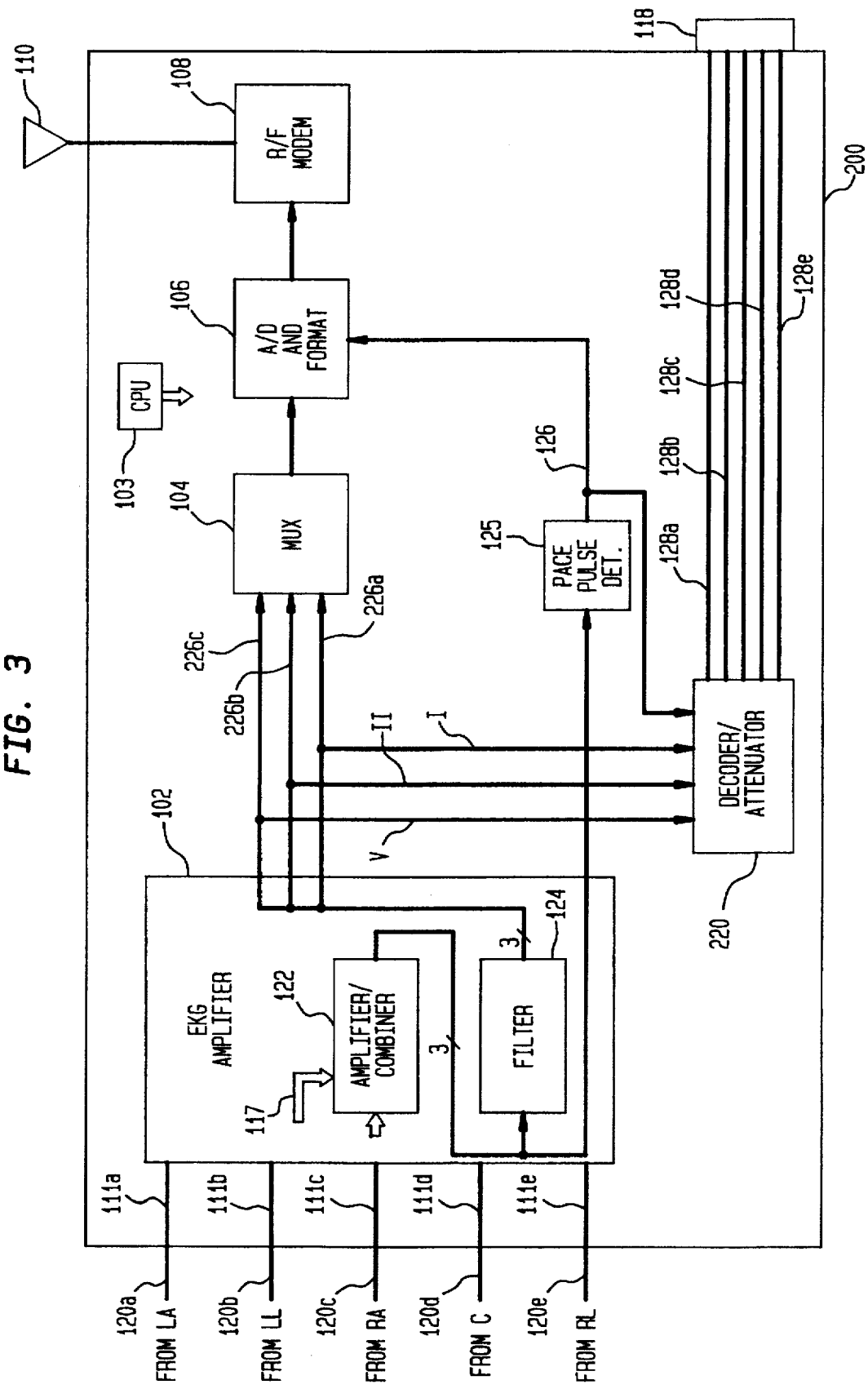
FIG. 3 is a block diagram of a second embodiment of the telemetry transmitter shown in FIG. 1.
Figure 4:
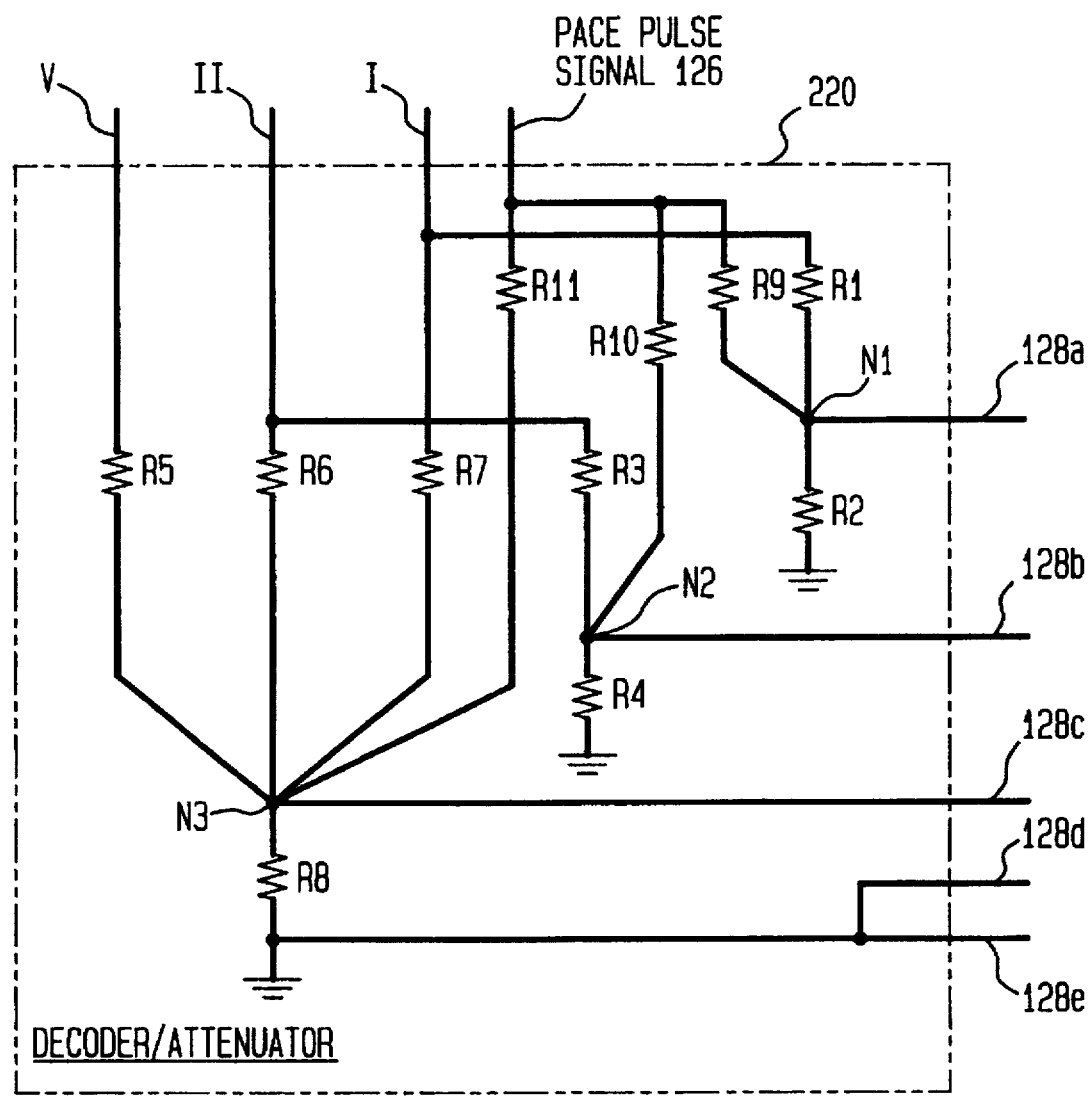
FIG. 4 is a block diagram of the decoder/attenuator circuit shown in FIG. 3.

FIGS. 2–4 show two exemplary embodiments of a telemetry transmitter 100 and 200 in accordance with the invention.

FIG. 2 is a block diagram of an exemplary embodiment of the telemetry transmitting apparatus 100 shown in FIG. 1. Transmitter 100 provides reception and wireless transmission of electrocardiogram (EKG) and pacemaker signals. The EKG signals are received from a plurality of electrodes LA, LL, RA, C and RL (shown in FIG. 1) coupled to the body of a medical patient by electrode wires 120a–e. The electrodes are coupled to the left arm (LA), left leg (LL), right arm (RA), chest (C) and right leg (RL) of the patient 10.

The EKG and pacemaker signals are received by transmitter 100 at a plurality of input terminals 111a–e. A plurality of buffers 112a–e are coupled to the input terminals 111a–e. Each buffer 112a–e receives a respective analog signal from a respective EKG electrode LA, LL, RA, C and RL. The terminals 111a–e and buffers 112a–e provide a means for receiving the plurality of analog signals representing the EKG signals. Each buffer 112a–e is an amplifier that has unity gain and unity feedback gain, with high input impedance and low output impedance. The buffers 112a–e hold the EKG data so that it may be provided to an EKG amplifier 102 and the analog output port 118. Buffers 112a–e are connected to output port 118 by a plurality of electrical couplings 116a–e and to EKG amplifier 102 by electrical connections generally indicated by arrow 117.

Other elements of the telemetry transmitter 100 may be the same type components as used in conventional telemetry transmitters. For example, EKG amplifier 102 includes an amplifier/combiner circuit 122 for boosting the EKG voltage signals, and for combining the input voltage signals received from buffers 112a–e into three EKG lead signals. In the exemplary embodiment, the gain of amplifier/combiner circuit 122 is 500. The amplifier/combiner circuit 122 forms the three leads from the five input voltage signals. The three leads are designated I, II, and V, which are the standard designations used in the field. Lead I is formed by the differential voltage between the left arm electrode LA and the right arm electrode RA, according to equation 1.

$$I = LA - RA \tag{1}$$

Lead II is formed by the differential voltage between the left leg electrode LL and the right arm electrode RA.

$$II = LL - RA \tag{2}$$

Lead V is formed by equation (3).

$$V = C - (LA + RA + LL)/3 \tag{3}$$

where: C, LA, RA and LL designate the signals returned by the respective chest, left arm, right arm and left leg electrodes.

Amplifier 102 also includes a filter 124 coupled to the output of amplifier/combiner circuit 122 for removing artifacts such as high-frequency noise (out of the frequency band of the EKG signal) from the EKG signal. Amplifier/combiner circuit 122 also removes any cardiac pacemaker pulse signals picked-up by the patient electrodes.

Therefore, a pace pulse detector 125 is coupled to also receive the output from amplifier/combiner circuit 122 for monitoring the EKG lead signals produced thereby for the presence of cardiac pacer pulses. Pace pulse detector 125 produces a digital pulse signal 126 if a cardiac pacer pulse is detected on one or more of the three lead signals. The pace pulse signal 126 can merely be a pulse indicating that a pacer signal has been detected, or a more elaborate signal which simulates the detected pacer pulse. The precise nature of the pace pulse signal developed by detector 125 is left to the designers' choice. Pace pulse detectors conventionally include a slew-rate detector to detect the rising or falling edges of a pacer signal. The construction and operation of pace pulse detectors are well known to those of ordinary skill in this technology, as shown, for example, by the pace pulse detector descriptions in U.S. Pat. Nos. 4,934,376, 5,231,990, 5,025,808 or 4,658,831. Thus, further description of detector 125 is not necessary.

As is also conventional in EKG monitoring apparatus, "lead-off" detection and switching circuitry may also be provided, as described, for example, in U.S. Pat. Nos. 5,231,990 or 5,025,808. In the illustrated FIG. 2 embodiment, a lead-off detector/switch 127 is coupled to each of electrical couplings 116a–e to monitor the outputs of buffers 112a–e to determine the sufficiency of electrical contact made by the EKG electrodes to the body of the patient, and control the connection of couplings 116a–e to output port 118 via couplings 128a–e. Each electrode signal lead is monitored to determine if an electrode has come loose and/or disconnected, and if a loose and/or disconnected electrode signal lead is found, a switch circuit portion of lead-off detector/switch 127 de-couples that electrode signal lead and in its place substitutes a lead having a good connection to the patient. For example, if monitoring of the RL signal on coupling 116e indicated that the RL electrode was loose and/or disconnected, the C signal from coupling 116d could be substituted therefor.

Wireless transmitting circuitry 103, 104, 106 and 108 may include conventional transmitting devices, coupled to the receiving circuitry 111a–e, 112a–e and 102, which form and transmit an output signal 50, representing the EKG and detected pace pulse signals, via a wireless coupling. In the exemplary telemetry transmitter 100, under the control of a central processing unit (CPU) 103 and via electrical signal connections indicated generally by arrow 130, a multiplexer 104 combines the EKG lead I, II and V signals into a single analog signal 105 that is applied to an analog to digital (A/D) converter and formatter 106. It is contemplated that multiplexer 104 may combine signals I, II and V using time-division multiplexing techniques or frequency division multiplexing techniques. A/D converter and formatter 106 is also responsive to the output signals of pace pulse detector 125 and lead-off detector/switch 127. Under the control of CPU 103 and via electrical signal connections indicated generally by arrow 130, a digital signal 107 is developed by A/D converter and formatter 106 which comprises a serial presentation of input data, such as the EKG lead data in a first data block, pacer data in a second data block and battery voltage and button status in third and fourth data blocks, respectively. Next, digital signal 107 is frequency modulated by an R/F modem 108 and then applied to an antenna 110 for transmission. The R/F modem 108 may include, for example, frequency shift keying (FSK) or quadrature amplitude modulation (QAM) circuitry.

Note, using the apparatus of FIG. 2, the signals received at the analog output port 118 are the same signals as those input to EKG amplifier 102.

FIG. 3 is a block diagram of a second exemplary embodiment of a telemetry transmitter 200 constructed in accordance with the invention, wherein the signals received at the analog output port 118 are not the same as those input to EKG amplifier 102, but signals reconstructed from the combined lead signals. Elements that are common between the two embodiments (102, 103, 104, 106, 107, 108, 110, 111a–e, 118, and 128a–e) have the same reference numerals as the corresponding elements in FIG. 2, for ease of identification. For brevity, the description of these common elements is not repeated. Additionally, a lead-off detector/switch similar to switch 127 shown and described in FIG. 2 is not shown in the FIG. 3 embodiment, but could be incorporated if desired.

As is apparent from the drawing, analog output port 118 does not receive unconditioned signals directly from the input terminals 111a–e, as is the case in the embodiment of FIG. 2. Instead, the EKG lead signals I, II and V from leads 226a–c and output 126 of pace pulse detector 125 are provided to a combination decoder/attenuator device 220, which separates the three lead signals into five analog output signals, 128a–e. The decoder/attenuator 220 decodes each one of the amplified signals I, II and V, and attenuates the resulting individual signals to form a plurality of individual attenuated signals 128a–e that are substantially equal in magnitude to the respective analog signal LA, LL, RA, C and RL from which the amplified signals I, II and V are formed. Additionally, decoder/attenuator 220 places the digital pace signal from output 126 of detector 125 into the five analog output signals 128a–e.

In the embodiment of FIG. 3, there may be very small differences between the values of output signals 128a–e and the actual EKG voltages, because the artifacts/high frequency signal components which are filtered out by filter 124 are not restored by decoder/attenuator 220. For example, the original cardiac pacemaker pulse signal is replaced by the digital pace signal 126 provided by detector 125.

FIG. 4 shows an exemplary embodiment of a circuit to perform the functions of decoder/attenuator 220. In the exemplary embodiment, the voltage of the right arm electrode RA is held at a reference potential (e.g., ground). With RA set to zero, equations (1) through (3) may be rewritten to separate out the left arm, left leg and chest components as follows:

$$LA = I \quad (4)$$

$$LL = II \quad (5)$$

$$C = V + (I + II)/3 \quad (6)$$

Additionally, all of the signals are reduced in magnitude by a constant factor that is equal to the gain of amplifier 102 (shown in FIG. 3). In the exemplary embodiment, EKG amplifier 102 has a gain of 500, so the decoder/attenuator 220 reduces all of the voltage signals by a factor of 0.002.

The exemplary decoder/attenuator 220 is a voltage divider circuit. Although any number of circuits may be designed to perform the functions described above, the voltage divider provides a particularly inexpensive solution for achieving the desired gain adjustment and performing the arithmetic operations defined by equations (4) through (6).

The left arm LA voltage is produced at node N1, between resistors R1 and R2. This portion of the voltage divider circuit implements equation (4), and performs the gain adjustment. In the exemplary embodiment, the desired gain is 0.002, so the ratio of R2/R1 is 0.002. Exemplary resistances are R1=100,000 Ohms, and R2=200 Ohms.

The left leg LL voltage is produced at node N2, between resistors R3 and R4. This portion of the voltage divider circuit implements equation (5), and performs the gain adjustment. In the exemplary embodiment, the desired gain is 0.002, so the ratio of R4/R3 is 0.002. Exemplary resistances are R3=100,000 Ohms, and R4=200 Ohms.

The Chest voltage is produced at node N3, between resistor R8 and the resistors R5, R6 and R7. This portion of the voltage divider circuit implements equation (6), and performs the gain adjustment. In the exemplary embodiment, the desired gain is 0.002, so the ratio of R8/R5 is 0.002, and R6/R8=R7/R8=1500. Exemplary resistances are R5=100,000 Ohms, R6=R7=300,000 Ohms and R8=200 Ohms.

Decoder/attenuator 220 includes resistors R9, R10 and R11 coupled between the output of pace pulse detector 125 and nodes N1, N2 and N3, respectively, for adding pace pulse signal 126 to the five analog output signals 128a–e. Exemplary resistance values for resistors R9, R10 and R11 are 200,000 Ohms each.

It is understood by one of ordinary skill in the art that the use of a voltage divider to perform these arithmetic functions is most accurate and effective when there is a high gain in amplifier 102, so that the resistors R1, R3, R5, R6 and R7 are all much larger than R2, R4 and R8. In the exemplary embodiment, there are more than two orders of magnitude between the larger resistors and the smaller resistors, which is sufficient to accurately perform the attenuation function.

It is also understood by one of ordinary skill in the art that any device coupled to receive one of the five signals LA, LL, RA, C and RL described has a high input impedance so that the device does not change the resistance ratios.

It is further understood that many other circuits or devices could perform these functions, although the cost is likely to be higher. For example, attenuators containing active devices could be used to perform the gain adjustment. Furthermore, the choice of which EKG electrodes are used as the reference potential may be varied. In the exemplary embodiment, the right arm RA and right leg electrodes RL are considered to be ground. It would also be possible to use the left arm and left leg as ground.

Although the invention has been described in terms of its applicability to EKG telemetry transmitters, it is understood that the invention may be practiced in telemetry transmitters that transmit other forms of medical patient data (e.g., EEG, blood pressure, saturated oxygen or temperature).

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed:

1. A portable patient monitoring apparatus adapted for being carried by a medical patient and having as its primary function the reception and then wireless transmission to a remote monitoring device of medical data acquired from the patient, and having a secondary function of also providing the medical data to an output port of the telemetry transmitter for facilitating local monitoring of the medical data, comprising:

receiving circuitry adapted for being coupled to said patient for receiving a plurality of analog signals representing a sensed condition of the patient;

wireless transmitting circuitry, including a signal processor and a wireless signal transmitter coupled to the receiving circuitry for forming an output signal representing the patient's condition and transmitting said output signal via a wireless transmission to a remote monitoring device;

an analog output port included as part of the wireless transmitting circuitry; and output means coupled to the receiving circuitry for providing a plurality of analog output signals representing the patient's condition to the analog output port of the wireless transmitting circuitry simultaneously with the transmission of said output signal to the remote monitoring device.

2. Apparatus in accordance with claim 1, wherein said analog signals include analog EKG signals, and wherein the receiving circuitry includes EKG amplifying means responsive to the analog EKG signals for developing amplified EKG signals.

3. Apparatus in accordance with claim 2, wherein:

said EKG amplifying means includes a filter means for filtering said analog signals to develop said EKG signals; and further including, a pacemaker pulse detector responsive to said analog signals before being filtered by said filter means for developing a pace pulse signal and providing said pace pulse signal to said wireless transmitting circuitry for being included in said output signal being transmitted.

4. Apparatus in accordance with claim 3, wherein:

said output means includes a lead-off detector/switch which is individually responsive to each of said analog signals for sensing an insufficient coupling of said receiving circuitry to said patient, and for providing a substitute analog signal to said analog output port in place of an insufficiently coupled analog signal.

5. Apparatus in accordance with claim 4, wherein:

said lead-off detector/switch develops a lead-off sense signal which indicates insufficient coupling of said receiving circuitry to said patient, and a signal conduction path is provided for coupling said sense signal to said transmitting circuitry for being included in said output signal being transmitted.

6. Apparatus in accordance with claim 1, wherein:

the receiving circuitry includes a plurality of buffers, each buffet receiving one of the plurality of respective analog signals acquired from the patient; and the output means includes means for coupling the buffers to the analog output port.

7. Apparatus in accordance with claim 6, wherein the receiving circuitry includes an amplifier coupled to the buffers, the amplifier amplifying each respective one of the plurality of analog signals.

8. Apparatus in accordance with claim 1, wherein;

said analog signals include analog EKG signals;

the receiving circuitry includes:

an amplifier coupled to the receiving circuitry, the amplifier amplifying each respective one of the plurality of analog signals to form a respective amplified signal, and means for combining the plurality of amplified signals to form a plurality of EKG lead signals;

the wireless transmitting circuitry includes:

a multiplexer coupled to receive the EKG lead signals which combines the EKG lead signals to form a single signal, an analog to digital converter which digitizes the single signal provided by the multiplexer, and a radio frequency modem which converts the digital single signal into a radio frequency signal for wireless transmission to said remote monitoring device; and the output means includes:

a voltage divider circuit coupled to receive the EKG lead signals, for decoding the EKG lead signals into a plurality of individual signals that represent the respective analog signals before their amplification by the amplifier by said receiving circuitry, circuitry.

9. A patient monitoring system, comprising:

telemetry transmitting apparatus, located in a first housing, adapted for being carried by a medical patient and having as a primary function the reception and then wireless transmission to a remote monitor of electrocardiogram (EKG) data acquired from the patient and having a secondary function of also providing the EKG data to an output port of the telemetry transmitting apparatus for facilitating transfer of the EKG data to an input port of a local monitor;

a remote monitor, located in a second housing, having an input port at which the wireless transmission of the EKG data from the medical patient are received for display;

wherein said telemetry transmitting apparatus comprises:

receiving circuitry adapted for being coupled to said patient for receiving a plurality of analog signals representing the EKG data;

transmitting circuitry, including a signal processor and a wireless signal transmitter coupled to the receiving circuitry for forming an output signal representing EKG data of the patient and transmitting said output signal via a wireless transmission to said remote monitor;

an analog output port included as part of the transmitting circuitry; and output means coupled to the receiving circuitry for providing a plurality of analog output signals representing the patient's EKG data to the analog output port of the transmitting circuitry simultaneously with the wireless transmission of said output signal to the remote monitor;

and further including an electrical cable connecting the analog output port of the transmitting circuit to the input port of the local monitor.

10. A patient monitoring system in accordance with claim 9, wherein said remote monitor comprises a central monitoring station including:

wireless communication means for receiving the output signal; and a central station monitor coupled to the wireless communications means for displaying EKG waveforms derived from the received output signal.

11. A patient monitoring system in accordance with claim 9, wherein:

said receiving circuitry includes a filter means for filtering said analog signals to develop said analog signals representing EKG data; and further including, a pacemaker pulse detector responsive to said analog signals before being filtered by said filter means for developing a pace pulse signal and providing said pace pulse signal to said transmitting circuitry for being included in said output signal being transmitted.

12. A patient monitoring system in accordance with claim 9, wherein:

said output means includes a lead-off detector/switch, which is individually responsive to each of said analog signals for sensing an insufficient coupling of said receiving circuitry to said patient, and for providing a substitute analog signal to said analog output port in place of an insufficiently coupled analog signal.

13. A patient monitoring system in accordance with claim 12, wherein:

said lead-off detector/switch develops a lead-off sense signal which indicates insufficient coupling of said receiving circuitry to said patient, and a signal conduction path is provided for coupling said sense signal to said transmitting circuitry for being included in said output signal being transmitted.

14. A patient monitoring system in accordance with claim 9, further including:

a pacemaker pulse detector responsive to said analog signals for developing a pace pulse signal and providing said pace pulse signal to said output means, and said output means including combining means for adding said pace pulse signal to said analog output signals representing EKG data which are provided by said output means to said analog output port.

15. A method for operating a telemetry transmitter adapted for being carried by a medical patient and having as a primary function the reception of medical data acquired from a plurality of sensor devices coupled to a medical patient, and for providing via wireless transmission multiple signals to a remotely located display device for displaying the medical data, and having a secondary function of also providing the medical data to an output port of the telemetry transmitter for facilitating transfer of the medical data to a local display device, the method comprising the steps of:

(a) receiving from the sensor devices a plurality of analog signals representing a condition of the patient, the receiving being performed by the telemetry transmitter;

(b) forming an output signal representing the medical data and transmitting said output signal to said remotely located display device via a wireless transmission; and (c) forming and transmitting a plurality of analog output signals representative of the analog signals recited in step (a) to the output port of the telemetry transmitter for use by the local display device located proximate to the telemetry transmitter simultaneously with the transmission of said output signal to the remotely located display device.

16. A method in accordance with claim 15, wherein the sensor devices are EKG electrodes, and:

step (a) includes the step of receiving a plurality of analog signals representing EKG signals;

step (b) includes the step of forming and transmitting an output signal representing the EKG signals; and step (c) includes the step of forming and transmitting a plurality of analog output signals representing the EKG signals.

17. A method in accordance with claim 16, further comprising the step of:

(d) connecting the output port of the telemetry transmitting apparatus to the local display device, for locally displaying the EKG signals.

18. A method in accordance with claim 16, wherein step (b) includes the steps of:

(1) amplifying the plurality of analog signals to form a plurality of amplified signals, (2) combining the plurality of the amplified signals to form a plurality of EKG lead signals, (3) multiplexing the plurality of EKG lead signals to form a single signal, and (4) modulating a radio frequency carrier with the single signal;

and the method further comprises the step of:

(f) transmitting the modulated signal from the telemetry transmitter to said remotely located display device via the wireless transmission.

19. A method in accordance with claim 18, including, between steps (1) and (2), the step of:

(1a) filtering the plurality of amplified signals to attenuate signal components having frequencies outside of a band of frequencies occupied by the EKG signals.

20. A method in accordance with claim 16, wherein step (c) includes the further steps of:

(3) sensing an insufficient coupling of one or more of said electrodes to said patient, and in response to said sensing providing a substitute analog signal to said output port in place of an analog signal received from an insufficiently coupled electrode.

* * * * *